(12) United States Patent  
Carpenter et al.

(10) Patent No.: US 10,209,129 B2  
(45) Date of Patent: Feb. 19, 2019

(54) OPTICAL MEASUREMENT OF THIN FILMS

(71) Applicant: Nanosys, Inc., Milpitas, CA (US)

(72) Inventors: Amanda Carpenter, Sunnyvale, CA (US); Robert Wilson, Palo Alto, CA (US); Ernest C. Lee, Palo Alto, CA (US); Alexander Puski, Los Gatos, CA (US)

(73) Assignee: Nanosys, Inc., Milpitas, CA (US)

( * ) Notice: Subject to any disclaimer, the term of this patent is extended or adjusted under 35 U.S.C. 154(b) by 18 days.

(21) Appl. No.: 15/862,954

(22) Filed: Jan. 5, 2018

(65) Prior Publication Data

US 2018/0195901 A1 Jul. 12, 2018

Related U.S. Application Data

(60) Provisional application No. 62/443,202, filed on Jan. 6, 2017.

(51) Int. Cl.
*G01J 3/02* (2006.01)
*G01J 9/02* (2006.01)
*G01J 3/443* (2006.01)

(52) U.S. Cl.
CPC .......... *G01J 3/0205* (2013.01); *G01J 3/0202* (2013.01); *G01J 3/443* (2013.01); *G01J 9/0246* (2013.01)

(58) Field of Classification Search
CPC ......... G01J 3/0205; G01J 3/443; G01J 3/0202
See application file for complete search history.

(56) References Cited

U.S. PATENT DOCUMENTS

| | | | | |
|---|---|---|---|---|
| 5,863,209 A | * | 1/1999 | Kim | G09B 5/02 |
| | | | | 348/373 |
| 6,610,973 B1 | * | 8/2003 | Davis, III | A61J 7/02 |
| | | | | 250/222.1 |
| 7,570,786 B2 | * | 8/2009 | Ateya | G06K 9/2027 |
| | | | | 221/129 |
| 8,215,557 B1 | * | 7/2012 | Reno | A61J 7/02 |
| | | | | 235/462.13 |
| 9,030,657 B2 | * | 5/2015 | Kuhn | G01B 11/26 |
| | | | | 356/124 |
| 9,199,842 B2 | | 12/2015 | Dubrow et al. | |
| 2007/0003274 A1 | * | 1/2007 | Sukenari | F16M 11/10 |
| | | | | 396/428 |
| 2017/0079885 A1 | * | 3/2017 | Thompson | A61J 7/02 |

* cited by examiner

*Primary Examiner* — Maurice Smith  
(74) *Attorney, Agent, or Firm* — Sterne, Kessler, Goldstein & Fox P.L.L.C.

(57) ABSTRACT

Embodiments of measurement apparatus for measuring the optical properties of a sample film are described. The measurement apparatus includes a first stage, a second stage, and an arm structure coupled to the second stage. The first stage includes an optical source and a block of transparent material. The block of transparent material includes a surface that supports a sample film. The second stage includes a plurality of layers and an optical detector. The arm structure is designed to translate the second stage with respect to the first stage.

20 Claims, 8 Drawing Sheets

OPTICAL MEASUREMENT OF THIN FILMS

CROSS-CITE TO RELATED APPLICATIONS

This application claims the benefit of U.S. Provisional Application No. 62/443,202, filed Jan. 6, 2017, the disclosure of which is incorporated by reference herein in its entirety.

FIELD

The present application relates to optical measurement of films, such as those containing light emitting quantum dots.

BACKGROUND

The problems typically associated with measuring the optical properties of thin films in a light-recycling platform are related to robustness and repeatability. In a typical measurement of this type, a film to be measured is inserted into a standard backlit display between a light-guide panel (LGP) and light-recycling films (e.g., Brightness Enhancement Films, or BEF's). Both the LGP and the BEF's are fragile and prone to scratching, dust, and marking, which significantly change the optical properties of the display. In addition, a standard display is not designed to be taken apart and put back together multiple times, whereas repeated assembly and disassembly is required for inserting films for measurement results. Each replacement of the film may result in a different alignment with each measurement. This variable alignment also changes the optical properties of the display. Finally, alignment of a calibrated measurement tool and the amount of ambient light also impact the measurements, and can result in additional variability.

SUMMARY

Embodiments of the present application relate to an apparatus and a method of using an apparatus to measure the optical properties of a sample film. The embodiments of the present application provide advantages over the traditional techniques for measuring certain optical properties of a sample film. In one example, the sample film includes a luminescent material such as, for example, a plurality of quantum dots (QDs) and the measured optical properties are related to the light generated by the luminescent material in the sample film.

According to an embodiment, an apparatus designed to measure optical properties of a sample film includes a first stage, a second stage, and an arm structure coupled to the second stage. The first stage includes an optical source and a block of transparent material. The block of transparent material includes a surface that supports a sample film. The second stage includes a plurality of layers and an optical detector. The arm structure is designed to translate the second stage with respect to the first stage.

According to an embodiment, a method of measuring the optical properties of a sample film includes placing the sample film onto a first stage and positioning a second stage onto the sample film using an arm structure coupled to the second stage. The second stage is positioned such that the sample film is sandwiched between the first stage and the second stage. The second stage has a given layer structure. The method further includes generating light via an optical source in the first stage and receiving light at a detector coupled to the second stage. The method also includes determining one or more optical properties of the sample film based on the light received by the detector.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present embodiments and, together with the description, further serve to explain the principles of the present embodiments and to enable a person skilled in the relevant art(s) to make and use the present embodiments.

The features and advantages of the present embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

Although specific configurations and arrangements may be discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications beyond those specifically mentioned herein.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to affect such feature, structure or characteristic in connection with other embodiments whether or not explicitly described.

Measurement Apparatus

Figure 1:
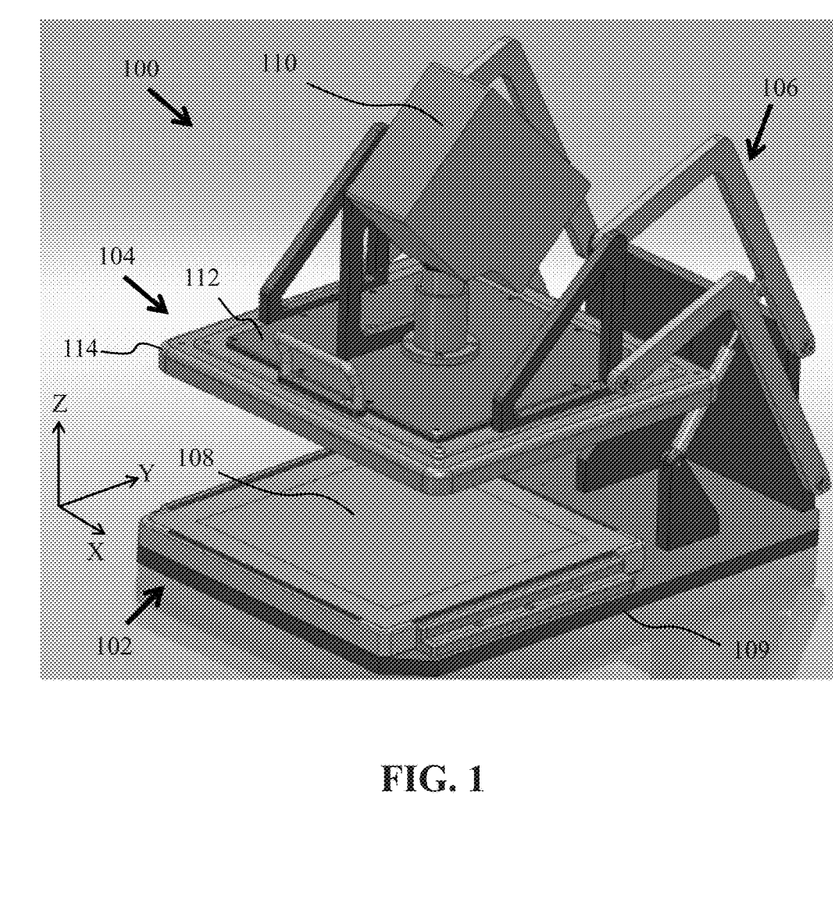
FIG. 1 illustrates a first view of a measuring apparatus, according to an embodiment.

FIG. 1 illustrates an example of a measurement apparatus 100, according to an embodiment. Measurement apparatus 100 includes a first stage 102, a second stage 104, and an arm structure 106 coupled to second stage 104. Measurement apparatus 100 may be designed to measure the optical properties of a sample film 108 placed over first stage 102. Measurement apparatus 100 may be designed to be used as a table-top instrument and thus may have dimensions of between about 20 centimeters and about 40 centimeters in the X-direction, and between about 30 centimeters and about 50 centimeters in the Y-direction. Measurement apparatus 100 may also include a base 109 to provide a weighted and solid foundation for the apparatus.

Measurement apparatus 100 may be designed to split the layers typically found in a backlit display that would use sample film 108 between first stage 102 and second stage 104. Due to the separation of the various layers between first stage 102 and second stage 104, a user can easily place and remove a film to be measured on first stage 102, while maintaining a consistent stacked layer structure once second stage 104 is translated downward onto first stage 102, sandwiching sample film 108 between first stage 102 and second stage 104. This is explained in more detail with reference to FIGS. 3A and 3B. Thus, high repeatability of measurements of the same film and between different films is maintained without performing any disassembly of measurement apparatus 100.

First stage 102 includes an optical source (shown and described in a later figure) to generate the light that impinges upon sample film 108, while second stage 104 includes an optical detector 110, according to an embodiment. Optical detector 110 receives light that has passed through sample film 108 (and/or light generated by QDs within sample film 108). This received light may be used to determine optical properties of sample film 108. The received light may be analyzed using a processing device within optical detector 110. In another example, optical detector 110 is connected wirelessly, or via a wired connection, to an external processing device (not shown). For example, optical detector 110 may use a USB connection to connect with a computer, where a processing device within the computer performs the analysis on the received light to determine one or more optical properties of sample film 108. In another example, optical detector 110 is not directly coupled to second stage 104, but receives light via one or more optical fibers that are coupled to second stage 104.

Optical detector 110 may comprise a spectrometer. In other examples, optical detector 110 comprises a conoscope or an imaging photometer. Other optical detector types are possible to use as well. Measurement apparatus 100 may be designed such that any optical detector can be coupled to second stage 104.

Second stage 104 may include a top cover 112 and a light shield 114 around the perimeter of second stage 104, according to an embodiment. Top cover 112 may comprise a metal, such as anodized aluminum. Top cover 112 may have an opening through which optical detector 110 is arranged to receive light. Light shield 114 may extend downward from the rest of second stage 104 along the perimeter of second stage 104 and may extend over the edges of first stage 102 when second stage 104 is brought into contact with first stage 102. In this way, any ambient light may be blocked from interfering with the optical measurement of sample film 108. Light shield 114 may comprise a metal or hard plastic material.

Arm structure 106 couples to second stage 104 and is arranged to translate second stage 104 relative to first stage 102, according to an embodiment. Arm structure 106 may include a plurality of structures that mechanically couple to various parts of second stage 104 as shown in more detail in FIGS. 2A and 2B. According to one embodiment, arm structure 106 is designed to steady second stage 104 and allow second stage 104 to translate along a path towards and away from first stage 102. The translation path may be only in the Z direction, or may have a first component in the Z direction and a second component in the Y direction. In yet another embodiment, arm structure 106 is designed to translate second stage 104 in all three cardinal directions.

Figure 2A:
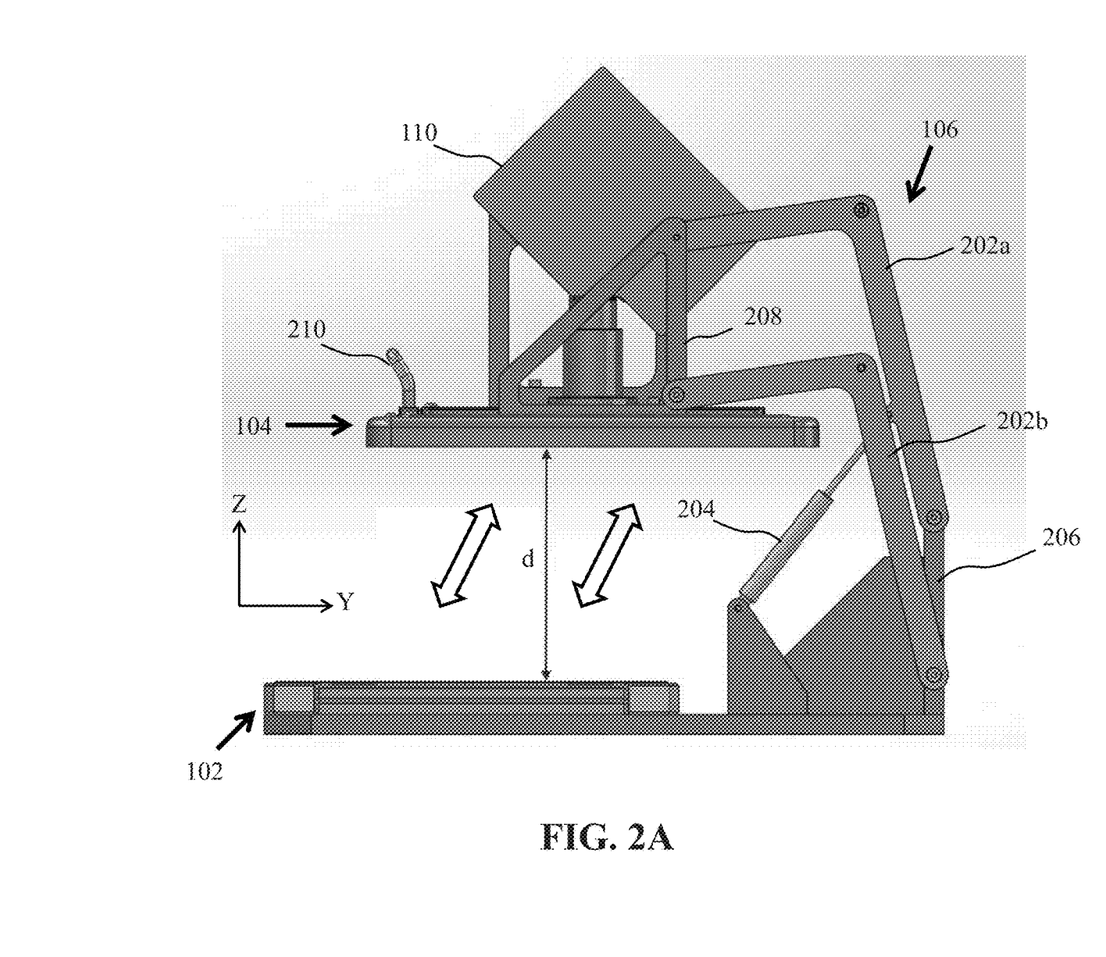
FIG. 2A illustrates a second view of the measuring apparatus with the second stage separated from the first stage, according to an embodiment.

FIG. 2A illustrates a side view of measurement apparatus 100, according to an embodiment. Arm structure 106 is illustrated with at least a first member 202a and a second member 202b coupling between second stage 104 and a base structure 206, according to an embodiment. First member 202a and second member 202b are examples of "L-shaped" beams as would be understood to person skilled in the relevant art. It should be understood that in this embodiment, similar members would also couple to the opposite side of second stage 104, such that four members in total couple between second stage 104 and base structure 206. In another embodiment, a single member couples between second stage 104 and base structure 206. Any arrangement of mechanical members may be used to couple between second stage 104 and base structure 206, as would be understood to a person skilled in the relevant art.

Second stage 104 may also include a handle 210. Handle 210 may provide a structure for a user to grip when raising or lowering second stage 104.

One or more of the members coupled between second stage 104 and base structure 206 includes an air spring 204, or any other known pneumatic actuator, according to an embodiment. In the illustrated embodiment, first member 202a is coupled to air spring 204. More than one air spring may be used. Air spring 204 may be designed to allow movement of arm structure 106 with some added resistance such that the movement is smooth and can be stopped anywhere along the range of motion of arm structure 106. Other types of springs may be used as well. According to an embodiment, this movement translates second stage 104 along a path identified by the double-ended arrows. Arm structure 106 may be designed to translate second stage 104 between a first position in contact with first stage 102 and a second position located a distance d above the surface of first stage 102. The maximum distance d will depend on the size and moveable range of arm structure 106. In one embodiment, distance d is at least 15 centimeters.

Figure 2B:
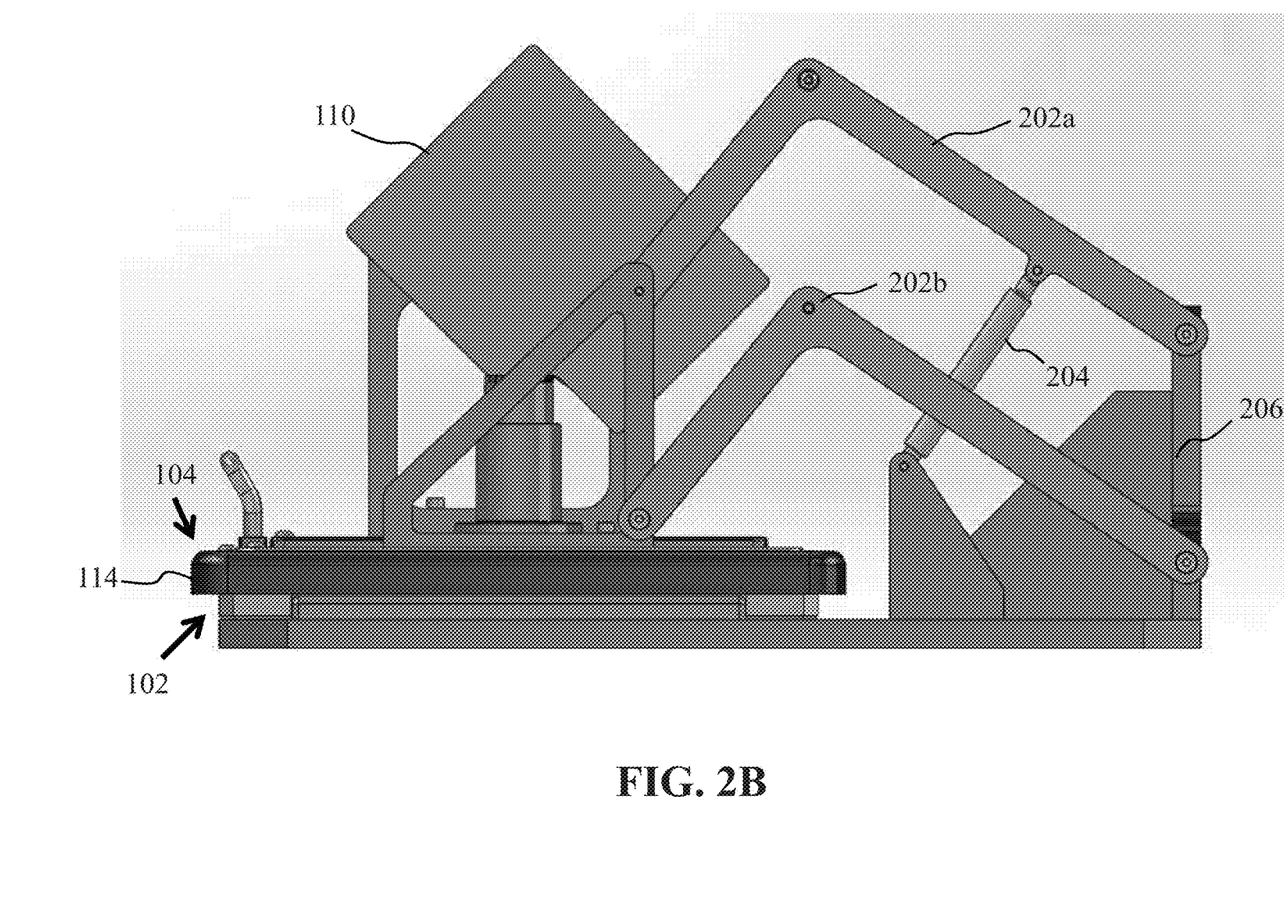
FIG. 2B illustrates the second view of the measuring apparatus with the second stage in contact with the first stage, according to an embodiment.

FIG. 2B illustrates the side view of measurement apparatus 100 with second stage 104 in contact with first stage 102, according to an embodiment. As can be seen in this view, light shield 114 extends around the outside edge of first stage 102 to substantially block all light from interfering with the optical measurements being made of the sample film sandwiched between first stage 102 and second stage 104. First member 202a and second member 202b have rotated about their respective connections to base structure 206 while air spring 204 is in a fully collapsed position to translate second stage 104 down into contact with first stage 102, according to an embodiment.

Figure 3A:
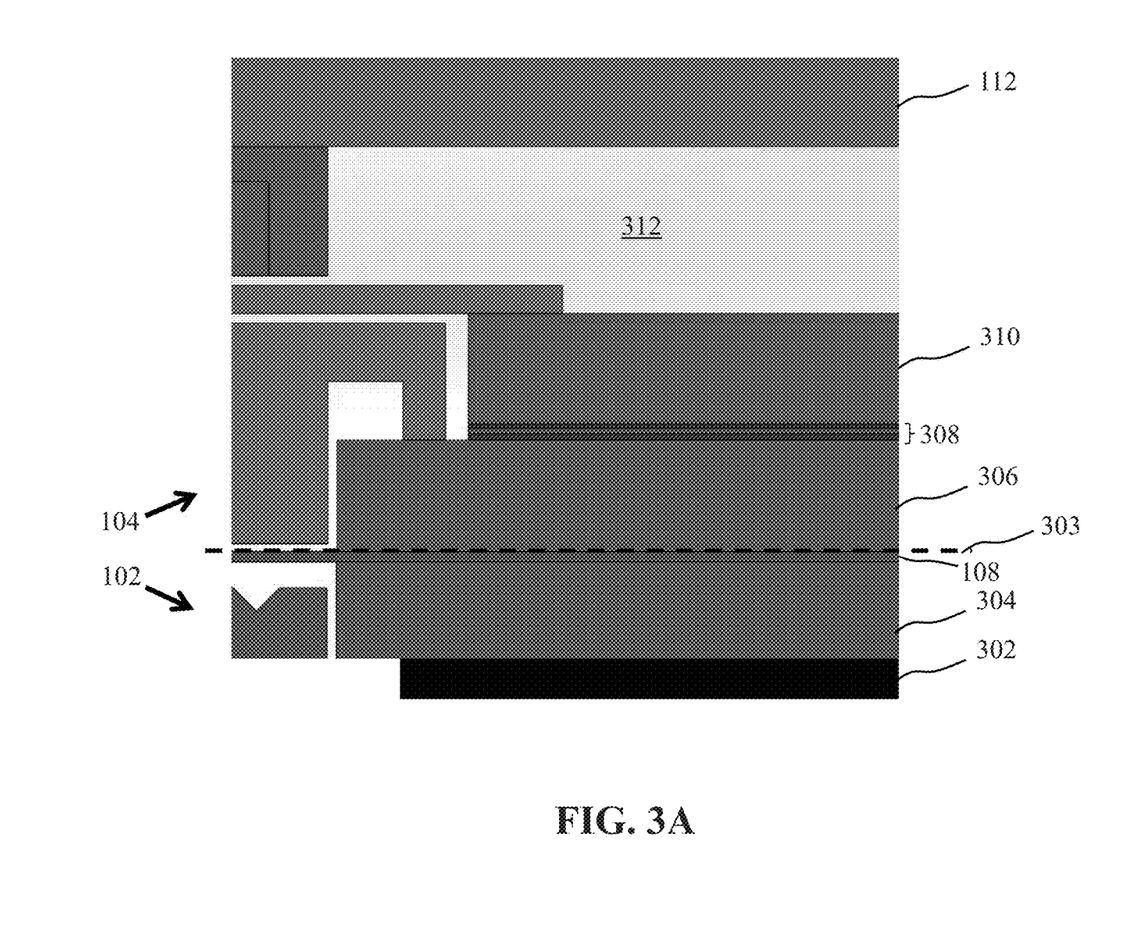
FIG. 3A illustrates a cross-section view of the first and second stages where the second stage is in contact with the first stage, according to an embodiment.

FIG. 3A illustrates a zoomed-in cross-section of first stage 102 in contact with second stage 104 to show the layer structure of each stage, according to an embodiment. Note that the thickness and any other geometrical properties of the various features are for illustrative purposes only and are not to be considered limiting.

First stage 102 includes an optical source 302, according to an embodiment. Optical source 302 may represent one source, or an array of discrete sources. Optical source 302 may be an array of light emitting diodes (LEDs). In one example, the light emitting diodes emit blue wavelengths of light. In another example, a white light source, or array of white light sources, is used. Any other light source may be used for optical source 302.

Above optical source 302, first stage 102 includes a first block of transparent material 304, according to an embodiment. First block of transparent material 304 may be glass that is substantially transparent to the light generated by optical source 302. In one embodiment, first block of transparent material 304 is B270 glass. First block of transparent material 304 may have a thickness ranging between about 2 mm and about 8 mm. In one example, first block of transparent material 304 has a thickness of about 5 mm.

Sample film 108 is placed over the top surface of first block of transparent material 304, according to an embodiment. Interface 303 is used to identify the boundary between those layers associated with first stage 102 and those layers associated with second stage 104. The movement of second stage 104 will move each of the layers above interface 303 with respect to the layers below interface 303.

Second stage 104 includes a second block of transparent material 306 that may be used to contact sample film 108, such that sample film 108 is sandwiched directly between first block of transparent material 304 and second block of transparent material 306, according to an embodiment. Second block of transparent material 306 may be glass that is substantially transparent to light generated by optical source 302 and/or light generated by QDs that may exist within sample film 108. In one embodiment, second block of transparent material 306 is B270 glass. Second block of transparent material 306 may have a thickness ranging between about 1 mm and about 5 mm. In one example, second block of transparent material 306 has a thickness of about 3 mm.

Second stage 104 also includes a plurality of layers 308, according to an embodiment. Plurality of layers 308 may include any combination of various brightness enhancing films (BEFs) and light diffuser layers. In one particular example, plurality of layers 308 includes a first BEF, a second BEF, and a diffuser layer.

One example of a brightness enhancing film is a light recycling film that reflects light having a certain angle of incidence back towards sample film 108 while allowing light having a different angle of incidence to pass through. This allows for the light that exits the light recycling film to have a certain direction of propagation that is more suitable for viewing and is commonly used in display technology. The light recycling film may comprise a molded polymer having a non-smooth surface to refract and reflect the light incident upon the surface depending on the angle of the light.

Plurality of layers 308 may also include a diffuser layer. The diffuser layer may be used to spread the light out before it is received by the optical detector. Examples of diffusers include thin film diffusers, ground glass diffusers, Teflon diffusers, opal glass diffusers, and greyed glass diffusers. Diffractive diffusers may be used as well, including gallium nitride or fused silica diffusers having processed rough surfaces.

Plurality of layers 308 are sandwiched between second block of transparent material 306 and a third block of transparent material 310, according to an embodiment. Third block of transparent material 310 may be glass that is substantially transparent to light generated by optical source 302 and/or light generated by QDs that may exist within sample film 108. In one embodiment, third block of transparent material 310 is B270 glass. Third block of transparent material 310 may have a thickness ranging between about 1 mm and about 5 mm. In one example, third block of transparent material 310 has a thickness of about 3 mm.

Top cover 112 may act as the top layer of second stage 104, according to an embodiment. Top cover 112 may be opaque to prevent light leakage or any external light from affecting the measurement of sample film 108. As illustrated in FIG. 1, top cover 112 may have an opening (not shown in FIG. 3A) through which an optical detector receives light. Top cover 112 may comprise anodized aluminum, or any other metal. In one embodiment, top cover 112 is suspended above third block of transparent material 310 by a gap 312. The height of gap 312 between top cover 112 and third block of transparent material 310 may be tailored based on the type of optical measurement being performed and/or the wavelengths of light being received by the optical detector.

Figure 3B:
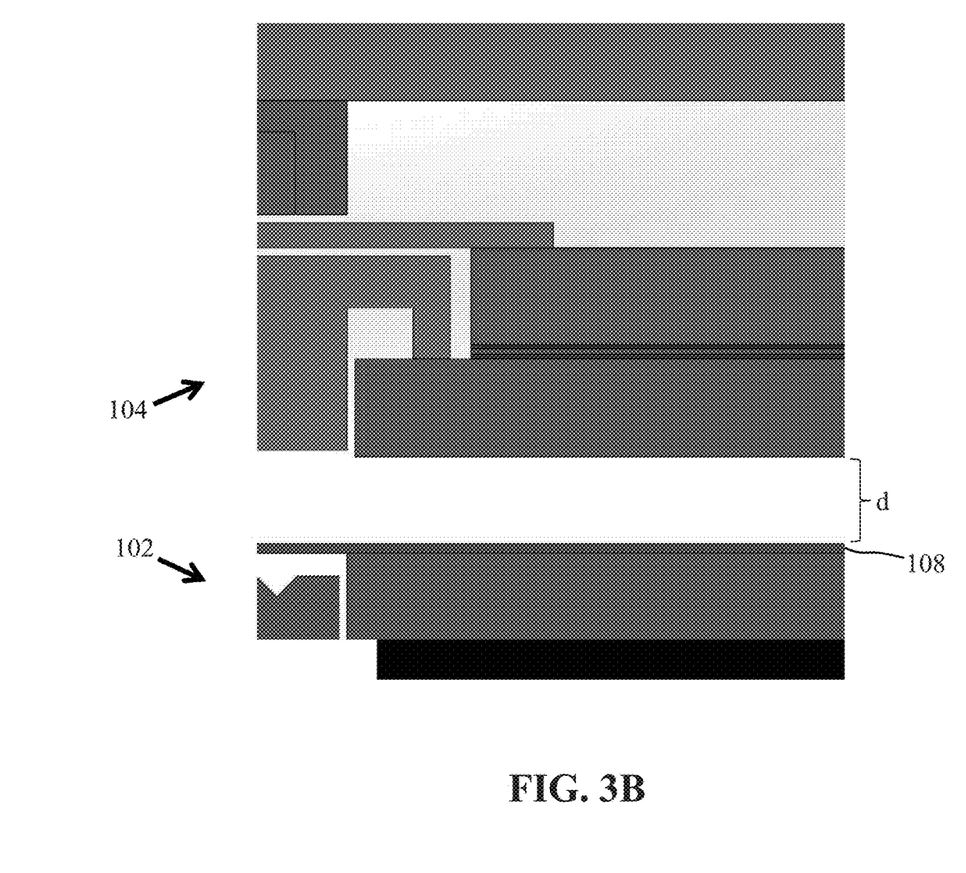
FIG. 3B illustrates a cross-section view of the first and second stages with the second stage separated from the first stage, according to an embodiment.

FIG. 3B illustrates a zoomed-in cross-section of first stage 102 separated from second stage 104 by a distance d, according to an embodiment. The distance d is provided between a top surface of sample film 108 and a bottom surface of second stage 104. Sample film 108 may be considered an element of first stage 102 when comparing separation distance between first stage 102 and second stage 104. The same layer structure as described in FIG. 3A is again illustrated in FIG. 3B.

Example Sample Film (Quantum Dot Enhancement Film)

Quantum dots (QDs) may be used in a variety of applications that benefit from having sharp, stable, and controllable emissions in the visible and infrared spectrum. Some display technologies involve the use of a quantum dot enhancement film (QDEF) where QDs are encapsulated in a polymer or other protective material that maintains the properties of the QDs and protects them from degradation. Such a QDEF may be an example of sample film 108 that can have its optical properties measured using measuring apparatus 100. QDs are one type of luminescent material that may be used in sample film 108. Other luminescent materials may include various phosphors, as an example.

Figure 4:
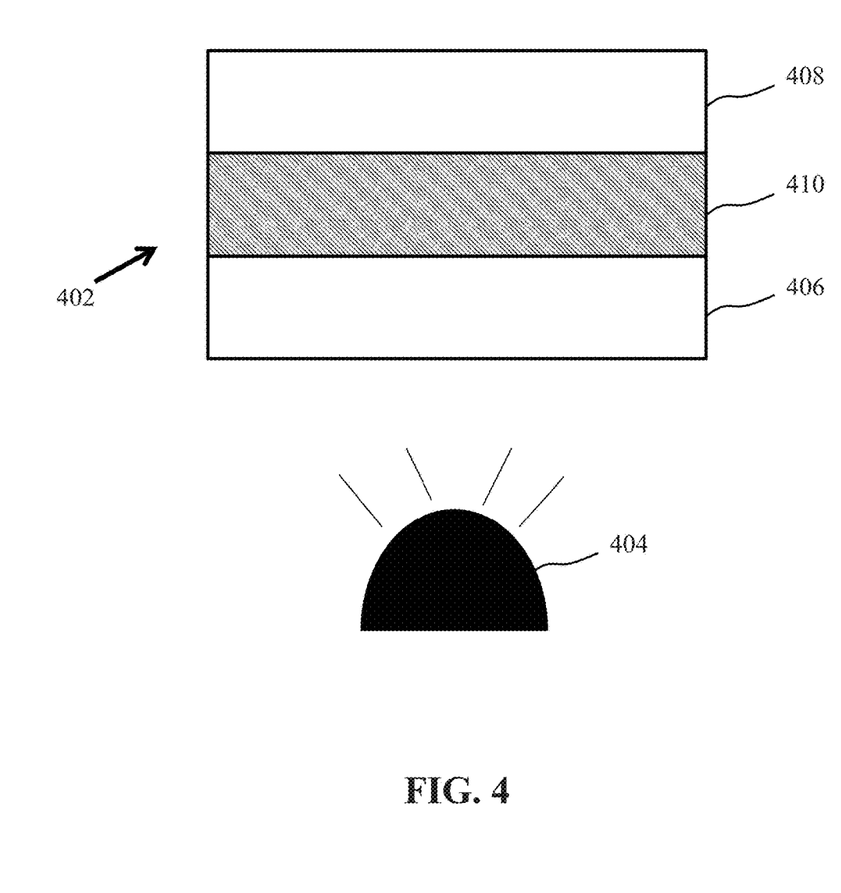
FIG. 4 illustrates a quantum dot enhancement film, according to an embodiment.

One example of a QDEF is illustrated in FIG. 4. QDEF 402 may include a bottom layer 406, a top layer 408, and a quantum dot layer 410 sandwiched between. Sample film 108 may be only quantum dot layer 410, or it may be the complete stack of bottom layer 406, top layer 408, and quantum dot layer 410.

An optical source 404 provides light from one side of QDEF 402 to excite the QDs within quantum dot layer 410 and cause them to luminesce. Optical source 404 may be similar to optical source 302 described above in measurement apparatus 100.

Bottom layer 406 and top layer 408 may be a variety of materials that are substantially transparent to the wavelengths being emitted by optical source 404 and to the wavelengths emitted by the QDs trapped within quantum dot layer 410. For example, bottom layer 406 and top layer 408 may be glass or polyethylene terephthalate (PET). Bottom layer 406 and top layer 408 may also be polyester coated with aluminum oxide. Other polymers may be used as well that exhibit low oxygen permeability and low absorption for the wavelengths being emitted by the quantum dots trapped within quantum dot layer 410. It is not necessary that bottom layer 406 and top layer 408 be comprised of the same material.

Quantum dot layer 410 includes a plurality of quantum dots within an adhesive material. According to an embodiment, quantum dot layer 410 has a thickness around 100 micrometers (μm) and is used as a light down conversion layer. The adhesive material binds to both bottom layer 406 and top layer 408, holding the sandwich-like structure together.

In an embodiment, the plurality of quantum dots includes sizes that emit in at least one of the green and red visible wavelength spectrums. The quantum dots are protected in quantum dot layer 410 from environmental effects and kept separated from one another to avoid quenching. The quantum dots may be spatially separated by enough distance such that quenching processes like excited state reactions, energy transfer, complex-formation and collisional quenching do not occur.

In one example, quantum dots are mixed within an amino silicone liquid and are emulsified into an epoxy resin that is coated to form quantum dot layer 410. Further details regarding the fabrication and operation of quantum dot enhancement films may be found in U.S. Pat. No. 9,199,842, the disclosure of which is incorporated by reference herein in its entirety.

Figure 5:
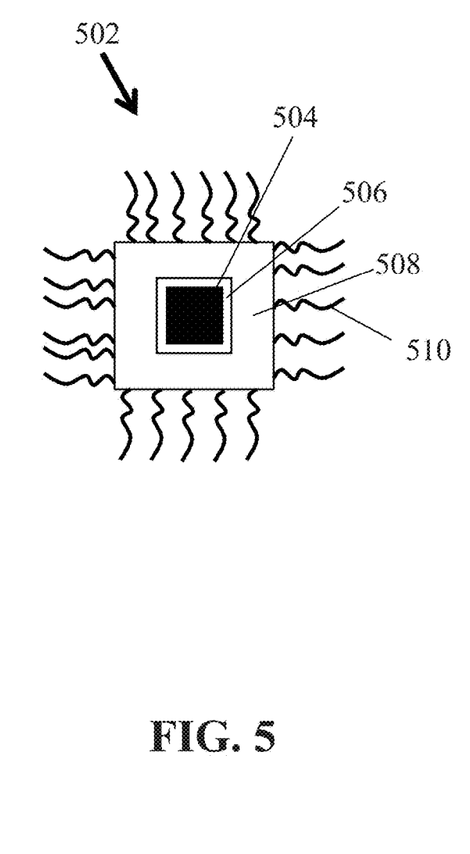
FIG. 5 illustrates the structure of a quantum dot, according to an embodiment.

FIG. 5 illustrates an example of the core-shell structure of a quantum dot 502, according to an embodiment. Quantum dot 502 includes a core material 504, an optional buffer layer 506, a shell material 508, and a plurality of ligands 510. Core material 504 includes a semiconducting material that emits light upon absorption of higher energies. Examples of core material 502 include indium phosphide (InP), cadmium selenide (CdSe), zinc sulfide (ZnS), lead sulfide (PbS), indium arsenide (InAs), indium gallium phosphide, (InGaP), and cadmium telluride (CdTe). Any other III-V, tertiary, or quaternary semiconductor structures that exhibit a direct band gap may be used as well. Of these materials, InP and CdSe are most often used, but InP is more desirable to implement over CdSe due to the toxicity of CdSe dust. CdSe may exhibit emissions having a full-width-half-max (FWHM) range of around 30 nm while InP may exhibit emissions having a FWHM range of around 40 nm.

Buffer layer 506 may surround core material 504. Buffer layer 506 may be zinc selenide sulfide (ZnSeS) and is typically very thin (e.g., on the order of 1 monolayer). Buffer layer 506 may have a wider band gap than core material 504, thus confining excitation to the core of quantum dot 502. Buffer layer 506 may have a lattice constant between that of core material 504 and shell material 508 to result in a smooth interface between core material 504 and shell material 508, therefore increasing the quantum efficiency.

Shell material 508 may be on the order of two monolayers thick and is typically, though not required, also a semiconducting material. The shell provides protection to core material 504. A commonly used shell material is zinc sulfide (ZnS), although other materials may be used as well without deviating from the scope or spirit of the invention. Shell material 508 may be formed via a colloidal process similar to that used to form core material 504.

Ligands 510 may be adsorbed or bound to an outer surface of quantum dot 502. Ligands 510 may be included to help separate (e.g. disperse) the quantum dots from one another. If the quantum dots are allowed to aggregate as they are being formed, the quantum efficiency drops and quenching of the optical emission occurs. Ligands 510 may also be used to impart certain properties to quantum dot 502, such as hydrophobicity, or to provide reaction sites for other compounds to bind.

Example Method of Operation

Figure 6:
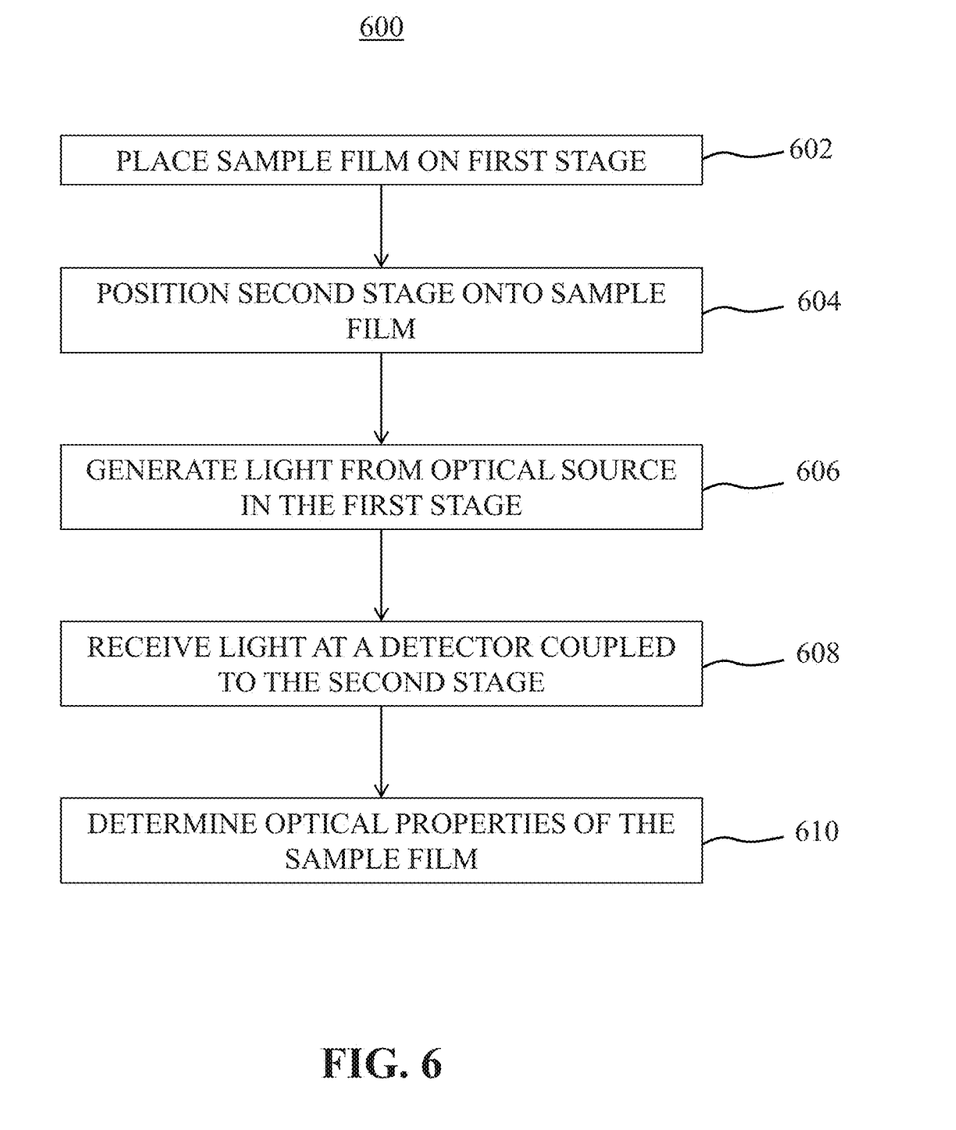
FIG. 6 illustrates an example method, according to an embodiment.

FIG. 6 illustrates an example method 600, according to an embodiment. Method 600 may be performed to measure the optical properties of sample film using an apparatus such as measurement apparatus 100. Method 600 is not intended to be exhaustive and other steps may be performed beyond those illustrated. Additionally, the various steps of method 600 may be performed in a different order.

Method 600 begins with step 602 where a sample film is placed on a first stage of a measurement apparatus. The sample film may be a quantum dot enhancement film (QDEF), or the sample film may include other luminescent material. The first stage may include a block of transparent material, and the sample film is placed on a top surface of the block of transparent material.

At step 604, a second stage is positioned (e.g., lowered) onto the sample film, according to an embodiment. The contact between the second stage and the sample film sandwiches the second film between the first stage and the second stage. In one example, the sample film is directly sandwiched between a first block of transparent material in the first stage and a second block of transparent material in the second stage. The second stage may be lowered onto the sample film (which, for the sake of completeness, may also be described as lowering the second stage onto the first stage) using an arm structure coupled to the second stage. The arm structure allows the second stage to translate between a first position separated from the first stage and a second position where the second stage is in contact with the first stage. Once the second stage has been lowered down onto the sample film, the stack of films and other layers that is created closely mimics that of a typical backlit display, according to an embodiment.

At step 606, light is generated from an optical source in the first stage. The optical source may be one source, or an array of discrete sources. The optical source may be an array of light emitting diodes (LEDs). In one example, the light emitting diodes emit blue wavelengths of light. In another example, a white light source, or array of white light sources, is used. The generated light impinges upon the sample film and may be partially absorbed by QDs within the sample film, thus causing the QDs to emit their own light of a longer wavelength.

At step 608, light is received by a detector coupled to the second stage. The received light may be light that was generated by the optical source and passed through the sample film. The received light may also include light that is generated by QDs within the sample film. The detector may be a spectrometer to detect and distinguish between a range of received wavelengths of light.

At step 610, optical properties of the sample film are determined. The detector is designed to convert the received light into an electrical signal that can be analyzed by a processing device to determine various optical properties of the sample film. Measured optical properties of the sample film include peak wavelength, full-width-half-max (FWHM), and brightness (e.g., of the QDs present in the sample film). Other measured optical properties may include the full spectra of the sample film and efficiency of the light conversion performed by the QDs of the sample film.

Example Test Results

A measurement apparatus such as measurement apparatus 100 was used to measure a set of nine sample films to determine repeatability of the measurements made for each sample film. Each of the sample films included red and green quantum dots sandwiched between polymer films. Each of the nine sample films was measured nine times using a first measurement apparatus and a second measurement apparatus over the course of a week, with each measurement apparatus being constructed as shown in FIG. 1, for a total of 162 measurements. The measured parameters for each of the films included chromaticity coordinates (x,y), luminance, and peak wavelength. Table 1 below provides the maximum deviation that occurred across the 162 measurements for each of the measured parameters, as well as the average standard deviation in the dataset for each measured parameter. This average standard deviation is also compared to the accuracy specifications of an industry-standard measurement tool (the PR-655 manufactured by Photo Research Inc.).

TABLE 1

| | Max deviation in 162 measurements | Average standard deviation for data set | PR-655 accuracy specifications |
|---|---|---|---|
| Chromaticity coordinates (x, y) | 0.0027 | 0.0003 | ±0.0015 |
| Luminance | 1.8% | 0.4% | ±2% |
| Peak wavelength | 0.5 nm | 0.1 nm | ±1 nm |

As can be seen from the data in Table 1, the measurement apparatus, as embodied in FIG. 1, provides highly consistent and stable measurements over time and between different units. When compared to the accuracy specifications of an industry-standard measurement tool, the measurement apparatus described herein outperforms the repeatability achieved with the industry-standard tool.

Final Remarks

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An apparatus configured to measure optical properties of a sample film, the apparatus comprising:
    a first stage comprising:
        an optical source, and
        a block of transparent material, wherein a surface of the block of transparent material is configured to support the sample film;
    a second stage comprising:
        a plurality of layers comprising at least one diffuser film,
        an optical detector, and
        a metal sheet disposed between the optical detector and the plurality of layers; and
    an arm structure coupled to the second stage, and configured to translate the second stage with respect to the first stage.

2. The apparatus of claim 1, wherein the plurality of layers comprises at least one light-recycling film.

3. The apparatus of claim 1, wherein the second stage further comprises a second block of transparent material such that the sample film is sandwiched directly between the block of transparent material and the second block of transparent material when the second stage is brought into contact with the first stage.

4. The apparatus of claim 3, wherein the second stage further comprises a third block of transparent material such that the plurality of layers are sandwiched between the second block of transparent material and the third block of transparent material.

5. The apparatus of claim 1, wherein the optical detector is a spectrometer.

6. The apparatus of claim 1, wherein the arm structure comprises a plurality of beams coupled to the second stage.

7. The apparatus of claim 1, wherein the arm structure is further coupled to one or more springs.

8. The apparatus of claim 1, wherein the optical source comprises one or more blue light emitting diodes.

9. The apparatus of claim 1, wherein the arm structure is configured to translate the second stage between a first position such that the first stage contacts the second stage and a second position such that the second stage is positioned apart from the first stage.

10. The apparatus of claim 1, wherein the second stage comprises a light shield around a perimeter of the second stage.

11. A method of measuring optical properties of a sample film, the method comprising:
    placing the sample film onto a first stage;
    positioning a second stage onto the sample film using an arm structure coupled to the second stage, such that the sample film is sandwiched between the first stage and the second stage, the second stage having an optical detector, a given layer structure with at least one diffuser film, and a metal sheet disposed between the optical detector and the given layer structure;
    generating light via an optical source in the first stage;
    receiving light at the optical detector; and
    determining one or more optical properties of the sample film based on the light received by the optical detector.

12. The method of claim 11, wherein the determining comprises determining a peak wavelength of light emission from the sample film when the sample film includes a luminescent material.

13. The method of claim 11, wherein the determining comprises determining a full-width half-max (FWHM) of a spectrum associated with the sample film when the sample film includes a luminescent material.

14. The method of claim 11, wherein the determining comprises determining a brightness of the sample film when the sample film includes a luminescent material.

15. The method of claim 11, wherein receiving light at the optical detector comprises receiving light generated by a luminescent material in the sample film.

16. The method of claim 15, wherein the luminescent material comprises a plurality of quantum dots.

17. The method of claim 11, wherein positioning the second stage comprises translating the second stage from a first position separated apart from the first stage to a second position where the second stage contacts the sample film.

18. The method of claim 17, wherein the first position is at least 15 centimeters above the first stage.

19. The method of claim 11, wherein the first stage includes a first block of transparent material, and the sample film is placed on the first block of transparent material.

20. The method of claim 19, wherein the second stage includes a second block of transparent material, and positioning the second stage comprises lowering the second stage onto the sample film such that the sample film is sandwiched directly between the first block of transparent material and the second block of transparent material.

* * * * *